United States Patent [19]

Cimino et al.

[11] Patent Number: 5,662,606

[45] Date of Patent: *Sep. 2, 1997

[54] CATHETER FOR ELECTROPHYSIOLOGICAL PROCEDURES

[75] Inventors: William W. Cimino, Temecula; Robert Abrams, Carlsbad; Miriam H. Taimisto, Anaheim Hills; Marc Jenson, San Marcos; Patrick E. Macaulay, Murrieta, all of Calif.

[73] Assignee: Heart Rhythm Technologies, Inc., Temecula, Calif.

[*] Notice: The term of this patent shall not extend beyond the expiration date of Pat. No. 5,364,352.

[21] Appl. No.: 339,125

[22] Filed: Nov. 14, 1994

Related U.S. Application Data

[63] Continuation of Ser. No. 31,249, Mar. 12, 1993, Pat. No. 5,364,352.

[51] Int. Cl.$^6$ ............................................. A61M 37/00
[52] U.S. Cl. ........................ 604/95; 604/264; 604/280; 128/642; 128/668
[58] Field of Search .................... 128/642, 668, 128/670, 695, 696, 699; 604/95, 264, 265, 280

[56] References Cited

U.S. PATENT DOCUMENTS

| | | |
|---|---|---|
| 3,605,725 | 9/1971 | Bentov . |
| 4,777,955 | 10/1988 | Brayton et al. . |
| 4,893,613 | 1/1990 | Hake . |
| 4,898,577 | 2/1990 | Badger et al. . |
| 4,920,980 | 5/1990 | Jackowski . |
| 5,037,404 | 8/1991 | Gold et al. . |
| 5,125,896 | 6/1992 | Hojeibane . |
| 5,156,151 | 10/1992 | Imran . |
| 5,170,787 | 12/1992 | Lindegren . |
| 5,178,159 | 1/1993 | Christian . |
| 5,188,111 | 2/1993 | Yates et al. . |
| 5,188,602 | 2/1993 | Nichols . |
| 5,190,050 | 3/1993 | Nitzsche . |
| 5,195,968 | 3/1993 | Lundquist et al. . |
| 5,199,433 | 4/1993 | Metzger et al. . |
| 5,281,213 | 1/1994 | Milder et al. ............ 604/95 X |
| 5,330,466 | 7/1994 | Imran ...................... 604/95 X |
| 5,364,352 | 11/1994 | Cimino et al. .................. 604/95 |
| 5,391,147 | 2/1995 | Imran et al. .................. 604/95 |
| 5,487,757 | 1/1996 | Truckai et al. ............ 604/95 X |

*Primary Examiner*—Robert A. Hafer
*Assistant Examiner*—N. Kent Gring
*Attorney, Agent, or Firm*—Fulwider Patton Lee & Utecht, LLP

[57] ABSTRACT

A catheter adapted to perform electrophysiological procedures comprises a body member, a manipulation handle attached to the proximal end of the body member for applying torque to the body member, the handle having a control knob adapted for control movements in a first plane and in a second plane simultaneously. A deflection control line is attached at its distal end to the distal portion of the catheter and its proximal end attached to the control device of the handle so that tension applied to the control line by sliding the control knob causes deflection of the distal portion of the catheter. A stiffening member is disposed within the body member of the catheter and is slidable, said stiffening member providing increased rigidity to the portion of the body member in which the stiffening member is located. Rotation of the control knob controls the position of the stiffening member in the body member. In a further aspect, a stiffening member in accordance with one embodiment includes a tapered distal end section with a ball formed on the distal tip, the tapered section terminating at the ball. In accordance with another aspect, the torsional rigidity of the catheter body is increased by use of a layer of aramid fibers mixed with an epoxy. In yet another feature, the handle and rotatable sliding element are symmetrically shaped to facilitate complete single-handed operation of the handle by the physician of all position control aspects of the catheter.

30 Claims, 5 Drawing Sheets

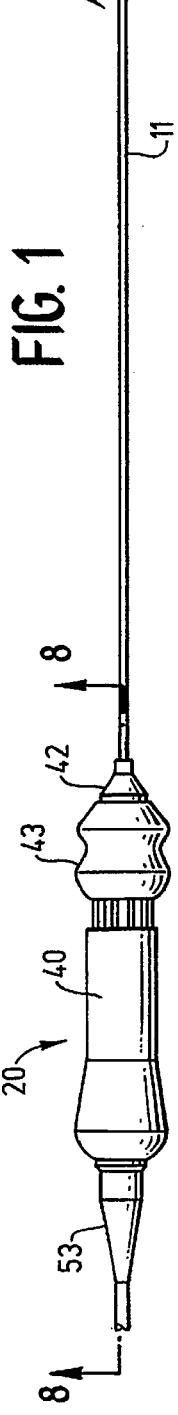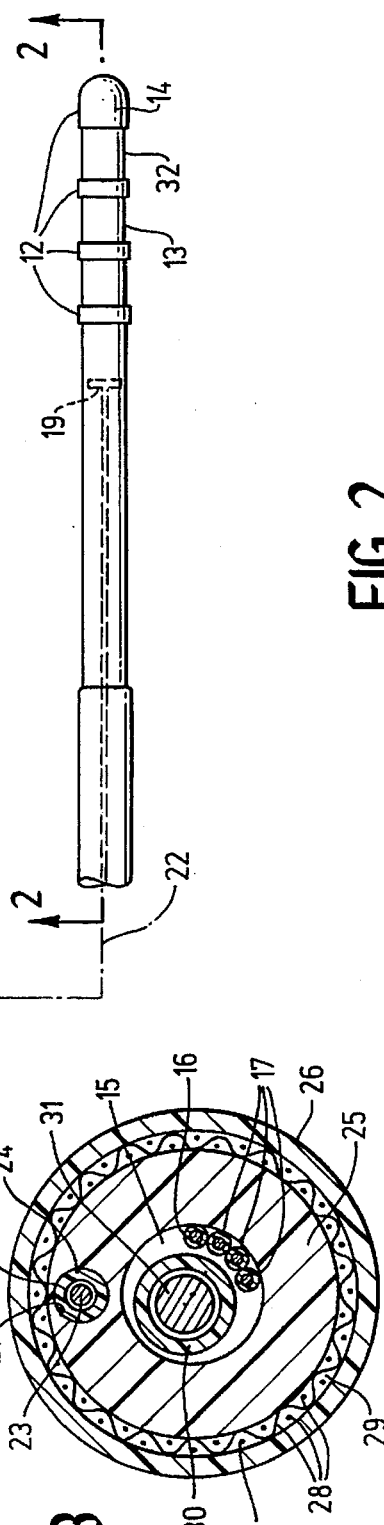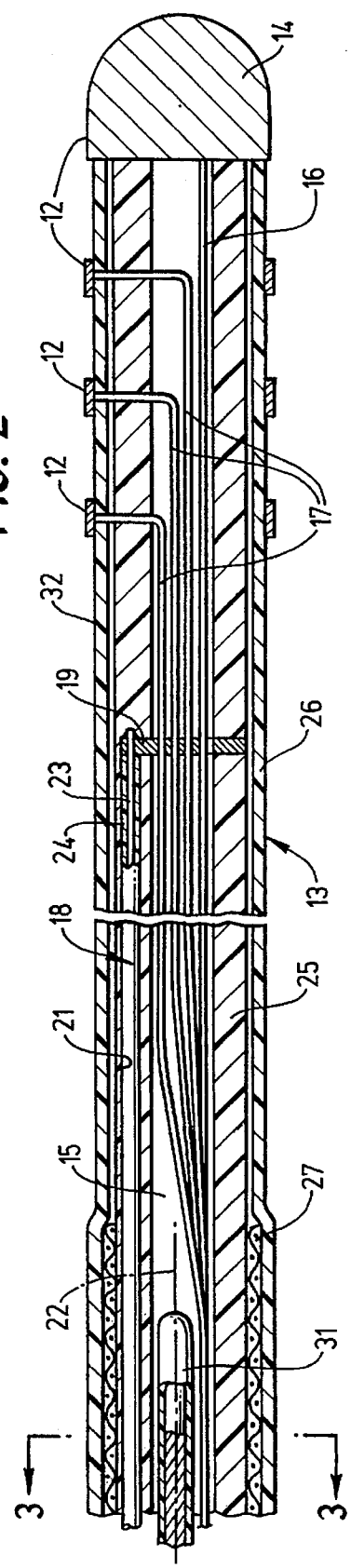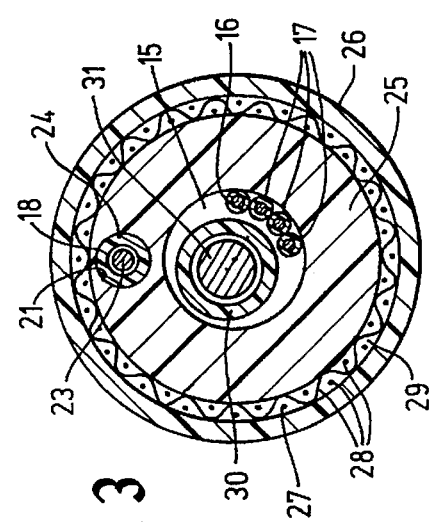

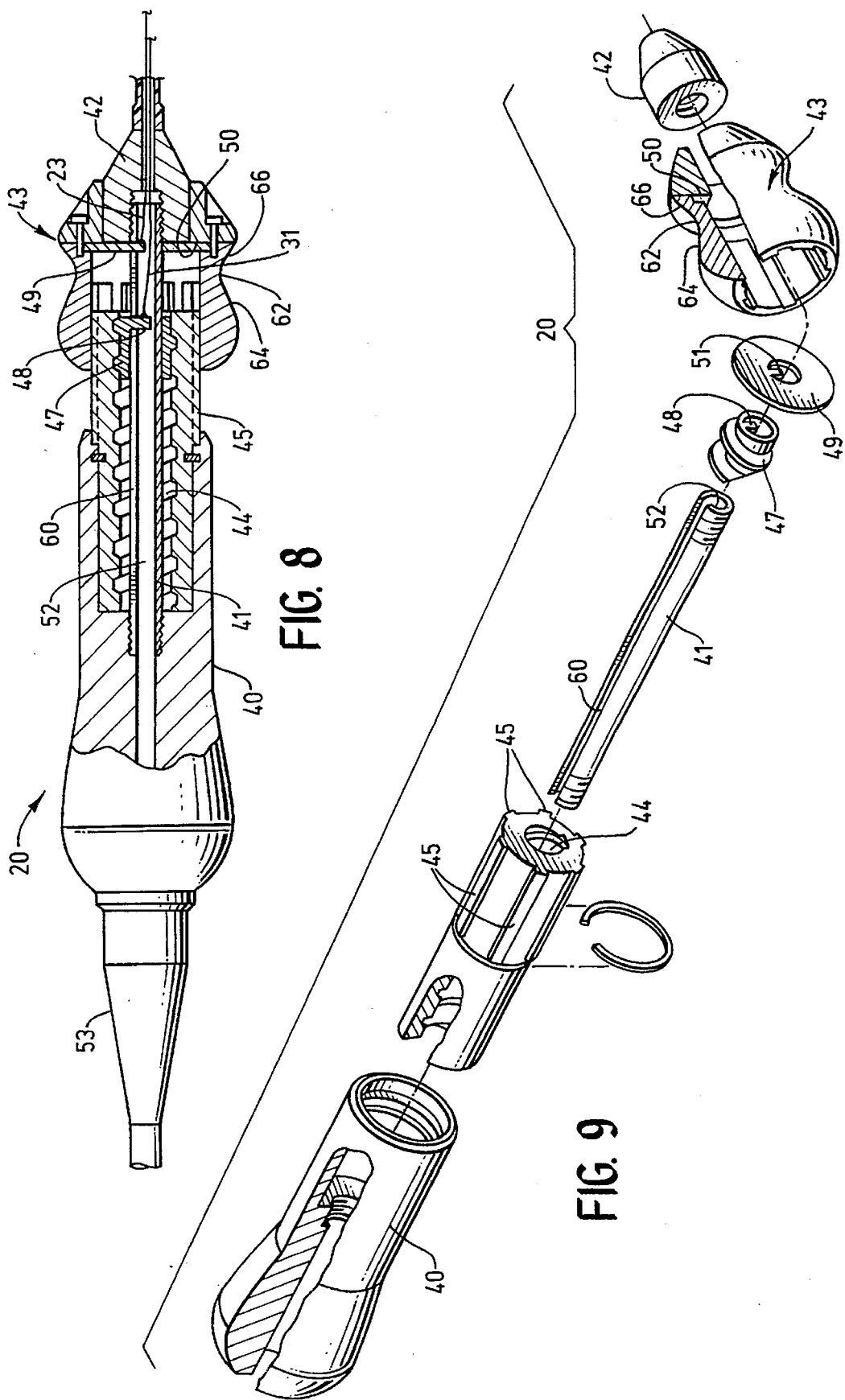

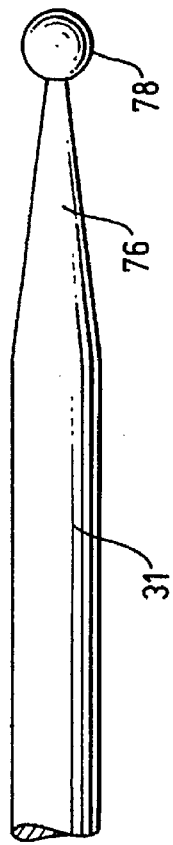
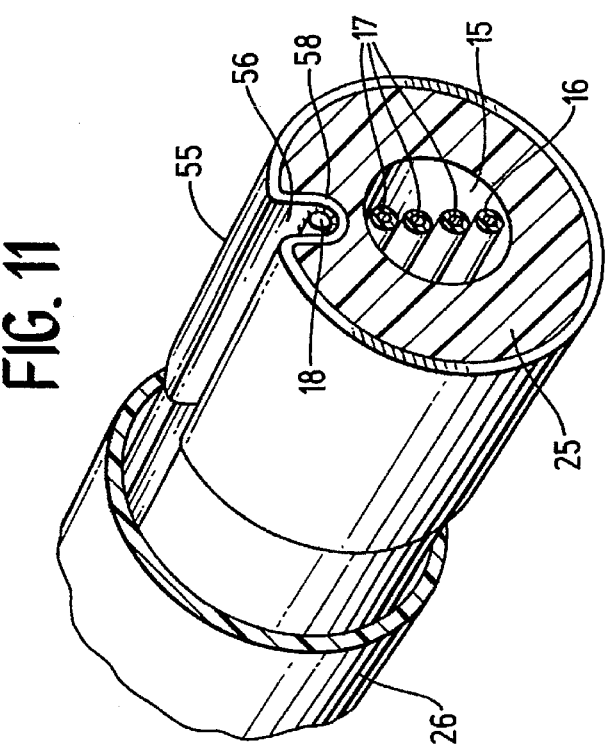
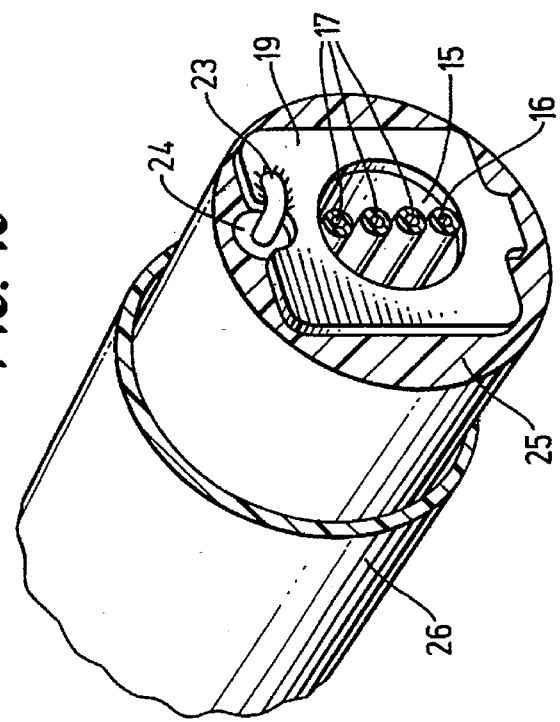

CATHETER FOR ELECTROPHYSIOLOGICAL PROCEDURES

This is a continuation of application Ser. No. 08/031,249, filed Mar. 12, 1993, now U.S. Pat. No. 5,364,352.

BACKGROUND

The invention relates generally to catheters, and more particularly, to steerable catheters for performing electrophysiological procedures, such as mapping electrical signals emitted from conductive cardiac tissue and ablating aberrant cardiac tissue at the point of arrhythmia origination in order to terminate the arrhythmia.

The heart beat in a healthy human is controlled by the sinoatrial node (S-A node) located in the wall of the right atrium. The S-A node generates action potentials which are transmitted through pathways of conductive heart tissue in the atrium to the atrioventricular node (A-V node) which in turn transmits the signals throughout the ventricle by means of the His and Purkinje conductive tissues. Improper growth of or damage to the conductive tissue in the heart can interfere with the passage of electrical signals from the S-A and A-V nodes resulting in disturbances to the normal rhythm of the heart, referred to as cardiac arrhythmia.

If the arrhythmia is refractory to medication, an alternative treatment is to ablate the aberrant conductive tissue. However, that aberrant tissue must first be located. One technique involves the electrical mapping of signals emanating from conductive cardiac tissue to locate the aberrant tissue causing the arrhythmia. Ablution may then be performed. Ablation of the aberrant conductive tissue usually controls the arrhythmia and allows the heart rhythm to return to an acceptable level.

One conventional method for mapping the electrical signals from conductive heart tissue is to provide an array of electrodes on the distal extremity of a catheter and place those electrodes in contact with the interior of a patient's heart. Typically, the catheter is introduced into the cardiovascular system of the patient through a blood vessel and advanced to an endocardial site such as the atrium or ventricle of the heart. When placed into the blood vessel, the catheter must follow the irregularly shaped path defined by the blood vessel and branch vessels until the distal end of the catheter reaches the desired location. To assist in steering the catheter, some catheters have a curved distal tip. While this pre-formed curve may fit the curves of some blood vessels, it rarely fits all anatomical possibilities. Greater freedom of movement is desirable.

To achieve greater control over the movement of the catheter in steering it through the cardiovascular system to the desired location in the patient, prior catheters have used guide wires to selectively vary the shape of the distal tip of the catheter. In another technique, a control line is attached at a point adjacent the distal tip of the catheter. Pulling the proximal end of the control line causes the distal tip of the catheter to bend in one direction. Other designs have used multiple control lines to obtain bending in multiple directions; however, the size of the catheter increases. Larger catheters are undesirable due to the difficulties involved in moving them through the patient's cardiovascular system and the increased blockage to blood flow. While the control line approach provides increased freedom of control over the movement of the distal end of the catheter, its effect in prior techniques is limited to an arc with a fixed radius.

In another technique, a mandrel or guide wire is also located in the catheter in addition to the control line and is moved to alter the radius of blend of the distal end of the catheter. The mandrel would be moved more towards the distal end or more towards the proximal end of the catheter to alter the radius of bend of the distal end. While such an approach has been found to yield improved control over the movement of the distal end, the disclosed technique required that the physician use two hands to exert this control. Additionally, no means were provided for holding the mandrel and control line in position once the desired bend was obtained thereby resulting in the physician having to hold both the mandrel end and the operating mechanism of the control line. Requiring the use of two hands for the steering function alone restricts the physician from performing other tasks at the same time.

Another consideration in keeping the catheter small in size but providing an increased steering capability is the torsional rigidity of the catheter. In catheters with low torsional rigidity, torsion may accumulate as the proximal end of the catheter is twisted by the physician. Then as the distal end finally begins rotating, the accumulated torsional moment will tend to unwind the catheter, resulting in rapid rotation of the tip inside the blood vessel. Such unwinding may result in the distal tip of the catheter overshooting the branch vessel entrance then requiring further steering manipulation on the part of the physician lengthening the procedure. Thus it is desirable to have increased torsional rigidity of the catheter so that rotating the proximal end of the catheter will result in immediate rotation at the distal end; i.e., immediate torque reaction.

A further consideration in navigating the catheter into the desired position in the patient is the bending rigidity or stiffness of the catheter. In some cases, increased force is required to advance the distal end of the catheter through a certain vessel position or to hold it against a particular site such as buttressing the catheter against a wall of the aorta or against a valve lip. However, decreased bending rigidity is beneficial in some cases. Therefore it would be desirable to provide variable bending rigidity of the catheter to provide increased steering and positioning control. Such a feature would be desirable in an electrophysiological procedure catheter due to the requirement for navigation completely into the heart and for continued contact with particular tissue during the beating action of the heart. Additionally, it would be desirable to incorporate the control means over the bending rigidity of the catheter into the same control device as is used for the other steering mechanisms.

Frequently, the position of the distal portion of the catheter within the heart may have to be adjusted one or more times in order to provide a complete and comprehensive view of the signals from the electrically conductive heart tissue which is necessary to detect the point where the arrhythmia originates. Once the origination point for the arrhythmia is determined, the conductive heart tissue at the site can be ablated. RF heating is one technique typically used for ablation. Successful ablation of the conductive tissue at the arrhythmia initiation site usually terminates the arrhythmia or at least moderates the heart rhythm to acceptable levels. Increased and easier control over the steering and positioning of the catheter would facilitate the mapping and ablation of the heart tissue.

Hence, those skilled in the art have recognized the need for a catheter for use in electrophysiological procedures which provides increased control over steering and positioning the catheter while not increasing the size of the catheter. It has also been recognized as desirable a catheter with increased torsional rigidity and a means for providing increased control over the axial rigidity of the catheter. The present invention fulfills these needs and others.

SUMMARY

Briefly and in general terms, the present invention is directed to a catheter which is adapted to perform electrophysiological procedures, such as detecting arrhythmia and ablating conductive pathways within a patient's myocardium in order to control arrhythmia. The catheter comprises a body member; a manipulation handle attached to the proximal end of the body member for applying torque to the body member, the catheter body being attached to the handle such that when the handle is rotated about its longitudinal axis, the body member rotates about its longitudinal axis in response. The handle also has a control device adapted for control movements in a first plane and in a second plane simultaneously.

A deflection control line is slidable in a direction parallel to the longitudinal axis of the body member and has its distal end attached to the distal portion of the catheter and its proximal end attached to the control device of the handle so that tension applied to the control line by movement of the control device in the first plane will cause the deflection of the distal portion of the catheter.

A stiffening member is disposed within the body member of the catheter and is slidable in a direction parallel to the longitudinal axis of the body member, said stiffening member providing increased rigidity to the portion of the body member in which the stiffening member is located. Additionally, the stiffening member is connected at its proximal end to the control device of the handle such that movement of the control device in the second plane controls the position of the stiffening member in the body member. In a further aspect, a stiffening member in accordance with one embodiment includes a tapered distal end section with a ball formed on the distal tip, the tapered section terminating at the ball. The tapered section permits easier bending of this portion of the stiffening member so that as it is advanced into the body member, it may negotiate a bend in a catheter which is already in position. The ball protects the body member of the catheter from being pierced by the stiffening member as the stiffening member is advanced and contacts a bend in the body member.

The deflection control line may be a wire or cable which is slidably disposed in the body member of the catheter. An open channel may be formed entirely within an inner tubular member of the body member, or may be formed in the exterior of the tubular member, and extends to the flexible distal portion of the catheter shaft where the distal end of the control line is attached. Tension applied to the control line by the physician operating the control device causes the flexible distal portion of the catheter shaft to be deflected from the central longitudinal axis of the catheter shaft and thereby allows the physician to control the shape of the distal extremity during the procedure which in turn facilitates steering through blood vessels and placement of the distal extremity against the cardiac tissue within the patient's heart. The anchoring element may be a plate fixed within a transverse plane in the distal portion of the catheter shaft or a cylindrical member disposed about the inner tubular member.

In accordance with another aspect, a torsion device for increasing the torsional rigidity of the catheter body is coupled with the body member of the catheter so that torque applied to the proximal end of the body member will be rapidly reflected at the distal end. In a further aspect, this torsional device comprises a layer of aramid fibers mixed with an epoxy, the layer being located within the body member such that rotating the handle results in rapid rotational response at the distal end of the catheter. Movement of the handle in a rotational sense controls the rotational position of the distal end of the catheter and movement of the handle in a longitudinal sense control the longitudinal position of the distal end of the catheter.

The handle control device may comprise a rotatable slide element, the rotation of which advances or retracts the stiffening element and the sliding action of which applies or releases tension on the control line. In another feature, the range of movement of the rotatable sliding element and the coupling of the control line thereto are selected to result in a complete release of tension on the control line when the rotatable sliding element is at one end of the range of sliding movement thereby permitting the body member to resume its substantially straight form. The range of movement caused by rotation of the rotatable slide element is also selected to permit positioning the stiffening member at a first position resulting in a first radius of curvature of the distal end of the body member when tension is applied to the control line, and at the other end of the range, in positioning the stiffening member at a second position resulting in a second radius of curvature of the distal end of the body member when tension is applied to the control line. The second radius of curvature is different from the first radius. At positions in between the respective ends of the ranges, various bends are possible and the bending of the distal end of the catheter is continuously variable between the ends of the ranges. In a further aspect, the positioning of the stiffening rod controls the bending stiffness of the body member and the range of movement of the control device is selected to achieve a predetermined range of bending rigidity.

In yet another feature in accordance with the principles of the invention, the handle and rotatable sliding element are symmetrically shaped to faciliate complete single-handed operation of the handle by the physician including rotation of the handle, longitudinal movement of the handle, rotation of the rotatable sliding element, and sliding of the rotatable sliding element. The handle itself may be rotated about its longitudinal axis while the sliding element is being both rotated and slid. Additionally, the handle is shaped for ease in grasping and retention by the physician's hand and further, the rotatable sliding element is shaped so that it may be both rotated and slid by the digits of that same hand. The sliding element in one aspect, has a groove formed about the outside and the two surfaces on either side of the groove are conveniently used by the operator to control sliding movement of the element.

The handle may also contain indicia, such as a colored band positioned on the handle body, to indicate movement of the rotatable slide element beyond a preselected point. The handle may also include gradations to provide a visual reference system to indicate the present position of the rotatable sliding element in its range of movement.

The catheter may have one or more electrodes on a distal portion, and may have an ablation electrode provided on the distal tip for ablation of cardiac conductive pathways. One or more electrical conductors extend with in the body member and are electrically connected to the electrodes on the distal portion of the catheter. Additional electrical conductors extend within the body member to electrically connect the ablation electrode to an electrical source, preferably a high frequency electrical source, for providing the ablation energy.

The catheter of the invention allows a physician to effectively control the shape and stiffness of the catheter during electrophysiological procedures, including the detection and ablation of aberrant conductive cardiac tissue. The catheter of the present invention can be more easily manipulated within a patient's heart and allows the physician to more accurately place the catheter electrodes as desired. Other aspects and advantages of the invention will become apparent from the following detailed description and accompanying drawings, illustrating by way of example the features of the invention.

BRIEF DESCRIPTION OF THE DRAWINGS

FIG. 1 is an elevation view of an electrophysiological catheter embodying features of the invention;

FIG. 2 is an enlarged longitudinal cross-sectional view of the distal portion of the catheter along lines 2—2 shown in FIG. 1;

FIG. 3 is a transverse cross-sectional view of the distal portion of the catheter shown in FIG. 2, taken along the lines 3—3;

FIG. 8 is an enlarged longitudinal view, partially in section, of a manipulating handle secured to the proximal end of the catheter as shown in FIG. 1;

FIG. 9 is an exploded perspective view of the manipulating handle shown in FIG. 8;

FIG. 10 is a perspective view of the distal portion of the catheter shown in FIG. 1 with the jacket and a distal extremity cut away to illustrate the connection of the deflection control line to the anchor plate;

FIG. 11 is a perspective view of the distal portion of an alternative catheter with the jacket and a distal extremity cut away to illustrate the connection of the deflection line to an anchor cylinder;

FIG. 13 is a view of the distal end of a tapered stiffening member having a ball formed on the distal tip.

DETAILED DESCRIPTION OF THE PREFERRED EMBODIMENTS

Figure 7:
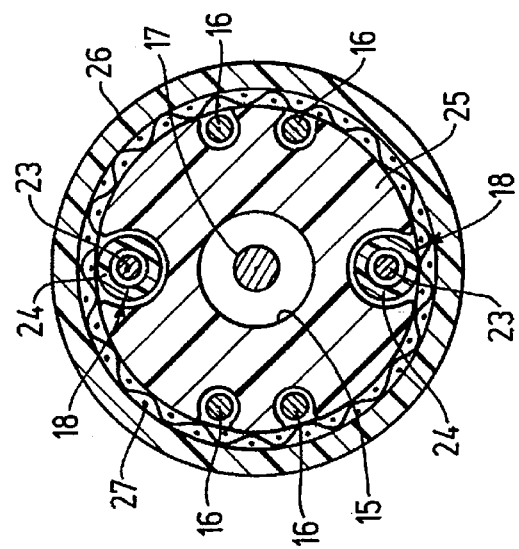
FIG. 7 is a transverse cross-sectional view of an alternative embodiment incorporating principles of the invention.

Referring now to the drawings with more particularity, wherein like reference numerals designate like or corresponding elements among the several views, there is shown in FIGS. 1–3, a catheter 10 usable for electrophysiological procedures and embodying features of the invention, including an elongated shaft or body member 11, a plurality of sensing electrodes 12 on the exterior of the body member along the distal portion 13 thereof and an ablation electrode 14 at the distal tip of the body member 11. The tip electrode functions both as an ablation electrode and as a sensing electrode; thus, both numerals 12 and 14 are pointing to it. The body member 11 has an inner lumen 15 which extends to the distal tip and which has disposed therein an electrical conductor 16 having a distal end electrically connected to the ablation electrode 14. Also extending within the inner lumen 15 are a plurality of electrical conductors 17 which have distal ends electrically connected to the sensing electrodes 12. Although three sensing electrodes 12 and one ablation electrode 14 are shown, this is for purposes of illustration only and is not meant to be restrictive of the invention. More or fewer of each of these electrodes may be used depending on the application. Additionally, the types of devices mentioned for sensing and ablation are for also only for purposes of illustration. For example, rather than using an "electrode" for ablation, a different type of energy transducer may be incorporated into the catheter.

The catheter body member 11 has a deflection control system 18 which has a distal end located at the distal portion 13 of the body member 11. The deflection control system 18 preferably comprises a control line or deflection wire 23 and a lubricous coating or jacket 24, e.g. a suitable fluoropolymer such as poly(tetrafluoro)ethylene which is available under the trademark Teflon® from E. I. duPont, deNemours & Company. Other fluoropolymers and other lubricous materials may be utilized to coat the deflection wire 23. The jacket 24 may be a lubricous sheath which allows for the movement of the deflection wire 23 therein. The deflection wire 23 is fixed to an anchor member 19 in the distal portion 13 so that, when tension is applied to the deflection wire 23 by means of the manipulating knob 43 mounted on the handle 20 at the proximal end of the catheter body member 11, the flexible distal portion 13 of the body member 11 will be deflected from its at rest position as shown in FIGS. 1 and 2 to the curved shape shown in FIG. 4. Preferably, the deflection control system 18 is disposed within a lumen 21 formed in the catheter body member 11 so as to be off-set from the central longitudinal axis 22 of the catheter body member 11 to more easily effect the deflection of the flexible distal portion 13. In the preferred embodiment shown in the figures, the body member 11 is constructed so that it is substantially straight when at rest and returns to that position when bending forces have been removed. The deflection control system 18 is used to impart such bending forces.

FIGS. 1 and 2 illustrate a presently preferred embodiment of the invention wherein the catheter body member 11 has an inner tubular member 25 with the inner lumen 15 extending therein, an outer jacket or coating 26 on the exterior of the body member and a reinforcing tubular structure or layer 27 disposed between the outer jacket or coating 26 and the inner tubular member 25. The layer 27 is formed of multi-filament strands 28 within a polymeric matrix 29. Preferably, the reinforcing multi-filament strands 28 are braided as shown schematically in FIGS. 3 and 7. It has been found that this construction provides improved torsion rigidity along the entire length of the body member 11 proximal to the relatively short, flexible distal portion 13. Thus, the torque developed by rotating the manipulation handle 20 at the proximal end of the body member 11 will be quickly communicated to the distal end and the torsion storage problems experienced in the prior art are lessened. The tubular reinforcing structure 27 terminates at a location proximal to the distal tip of the body member 11 to provide the deflectable distal portion 13 with more flexibility.

A mandrel or stiffening member 31 is slidably disposed within a sheath 30, preferably formed of a fluoropolymer such as Teflon, both of which are disposed in the inner lumen 15 of the inner tubular member 25. The stiffening member is preferably formed of stainless steel, although other materials may function as well. The advancement of the stiffening member 31 within the distal portion 13 of the catheter body member 11 controls the stiffness of the distal portion and in conjunction with the deflection wire 23 controls the shape of the flexible distal portion as shown in FIGS. 4-6.

Figure 4:
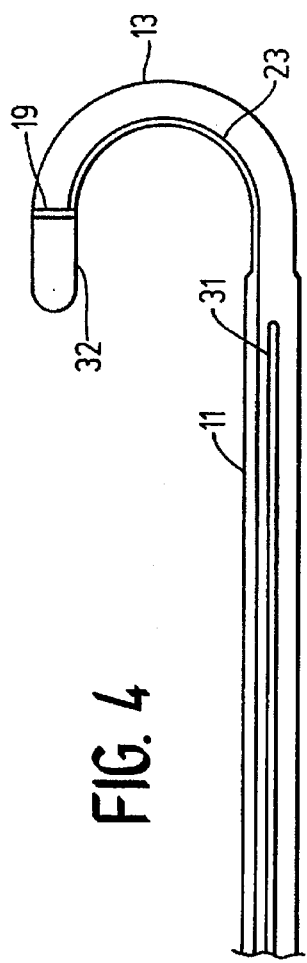
FIG. 4 is a schematic elevation view of a distal portion of the catheter shown in FIG. 1 with tension applied to a control line which extends into the distal portion of the catheter.

In FIG. 4 the stiffening member 31 is shown completely withdrawn from the distal portion 13 of the catheter body member 11 so that tension applied to the deflection wire 23 will result in the curvature of the distal portion 13 as shown. In the case shown in FIG. 5, the stiffening member 31 has a tapered end thus making that section more "bendable" and has been advanced into the distal portion 13. The tapered part of the stiffening member 31 has been bent and the curvature of the distal portion 13 is altered. Two radii of curvature are shown thus resulting in increased steering capability.

Figure 6:
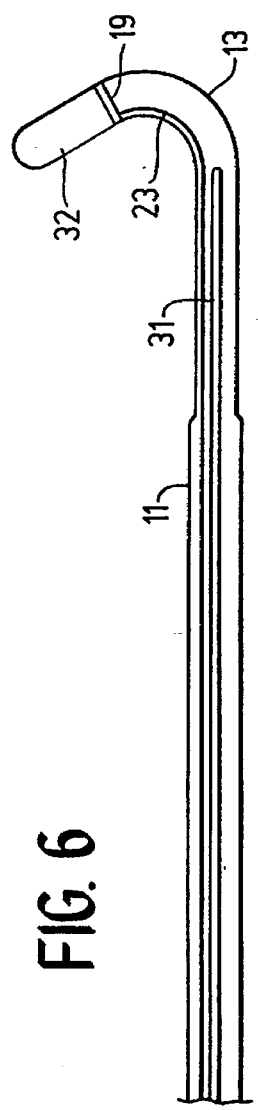
FIG. 6 is a schematic elevation view of a distal portion of the catheter similar to that shown in FIG. 5 except that the stiffening rod is advanced farther into the distal portion of the catheter than that shown in FIG. 5.

As depicted in FIG. 6, the stiffening member 31 is more stiff and had been advanced even farther into the distal portion 13 of the body member 11. The curvature is altered again. The portion 32 of the body member which extends distal to the location of the anchor member remains essentially straight.

Figure 5:
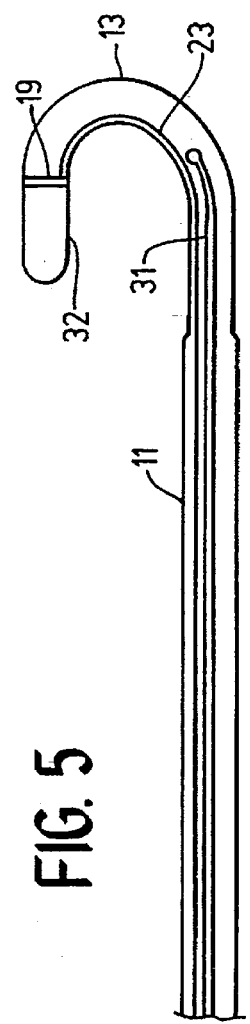
FIG. 5 is a schematic elevation view of a distal portion of the catheter similar to that shown in FIG. 4 except that a stiffening rod is advanced into the distal portion of the catheter shaft in addition to tension being applied to the control line.

FIG. 13 presents an enlarged view of the stiffening member 31 of FIG. 5. In accordance with this embodiment, the stiffening member 31 includes a tapered section 76 ending at a ball 78. The ball 78 will protect the catheter body from being pierced by the stiffening member from the inside such as in the case where the catheter has already been put into a curved configuration and the stiffening member is being advanced into that curved section of the catheter to obtain increased bending stiffness distally. Such may occur where the distal section 32 of the catheter will not remain in position against certain tissue due to heart movement. Rather than piercing the body member, the rounded distal tip of the stiffening member Will negotiate the curve of the body member. The remainder of the stiffening member 31 will then follow. The tapered section 76 likewise assists the stiffening member 31 in negotiating already established bends in the catheter. Because the tapered section is of a smaller diameter, it will bend more easily thus enabling the distal end of the stiffening member to bend around the existing catheter bend more easily. As mentioned above, a further advantage of the tapered section/ball combination is shown in FIG. 5 where different radii of bends are possible thereby giving the physician greater steering control.

The deflection wire 23, the stiffening member 31, and the torque control layer 27 resulting in additional torsional rigidity, allow the physician using the catheter to more easily and accurately advance the catheter through a patient's vascular system into the beating heart. The physician can more easily adjust the shape and stiffness of the distal portion 13 of the catheter 10 to place the distal portion at a desired location against a ventricle wall for example in a desired orientation. This degree of control provides the physician with greater versatility in accurately plating the catheter at the desired location in order to better determine the site from which the arrhythmia originates and to more accurately place the ablation electrode against the originating site of the arrhythmia to effectively ablate the conductive tissue at the site to eliminate or moderate the arrhythmia while the heart is beating. The position of the stiffening member 31 may be adjusted to result in greater or lesser bending stiffness as required. For example, when the catheter is placed against a beating heart and increased bending stiffness is needed to keep it in position, such stiffness may be attained by advancing the stiffening member towards the distal end of the catheter. Where less bending stiffness is required, the stiffening member may be retracted towards the proximal end of the catheter.

FIG. 7 illustrates an alternative embodiment to the catheter body member 11 construction shown in FIGS. 1—3. In this embodiment, the inner tubular member 25 is provided with a plurality of open channels formed in its exterior which are adapted to receive the electrical conductors 16 in addition to a plurality of deflection control systems 18. In this embodiment four sensing electrodes are provided on the distal portion of the catheter. The electrical conductor 17 connected to the ablation electrode 14 is shown extending through the central inner lumen 15. However, it may be disposed within a different channel which may be formed in the exterior of the tubular member 25 in order to provide a stiffening member within the inner lumen 15 as in the previously discussed embodiment. The channels are closed by the tubular layer 27.

The details of the manipulating handle 20 on the proximal end of the catheter 10 are shown in detail in FIGS. 8 and 9. The handle 20 generally includes a body 40, a tubular body member 41 having a proximal end seated within a recess provided within the body. A slide element 43 is slidably mounted about the cap 42 and an elongated female threaded element 44 which acts as a nut and which rotates within the body 40. The distal portion of the female threaded element 44 is provided with a plurality of longitudinally extending ridges 45 on the exterior thereof which are adapted to be slidably received within the interior surface of the slide element 43. Therefore, rotating the slide element 43 will cause rotation of the threaded element 44. A hollow male threaded element 47 is slidably disposed about the body member 41 and is threadably engaged within the female threaded element 44. The male threaded element 47 has an inward projection 48 to which the proximal end of the stiffening elements 31 is suitably secured such as by crimping or insert molding. A ring 49 is seated within a shoulder 50 provided on the interior of the slide element 43 and the ring 49 has an inward projection 51 to which is secured the proximal end of the deflection wire 23. In the preferred embodiment, the shoulder is formed by two parts fastened together by screws as shown in FIG. 8. The inward projections 48 and 51 are located in the longitudinal slot 60 in the shaft 41, and are thus restricted from rotating. The proximal end of the catheter body member 11 is secured to the cap 42 such as by adhesive. Therefore, rotating the handle 20 will result in rotation of the body member 11.

Longitudinal movement of the slide element 43 in the proximal direction by an operator will move the ring element 49 longitudinally in the proximal direction causing tension to be applied to the deflection wire 23 which is secured to the inward projection 51 of the ring 49 and thereby curves the distal portion 13 of the catheter body member 11. Longitudinal movement in the distal direction will lessen the tension applied to the deflection wire 23 and allow the distal portion 13 to return to its normal shape, which is usually straight. The slide element 43 includes a groove 62 into which the digit or digits of the operator may reside when moving the element. The surfaces 64 and 66 on either side of the groove would be used to receive the force applied by the operator's digits to move the slide element 43. This results in more positive control over the slide element and increased convenience in operation.

Rotation of the slide element 43 by the operator will rotate the female threaded element 44, which in turn will move the hollow male threaded element 47 along the body member 41 and result in the longitudinal movement of the stiffening member 31 which is connected to the inward projection 48 on the male threaded element 47. The stiffening member 31 must have sufficient column strength to communicate the thrust applied to the proximal end to the distal end thereof and to otherwise stiffen the distal portion 13 of the catheter body member 11.

Figure 12:
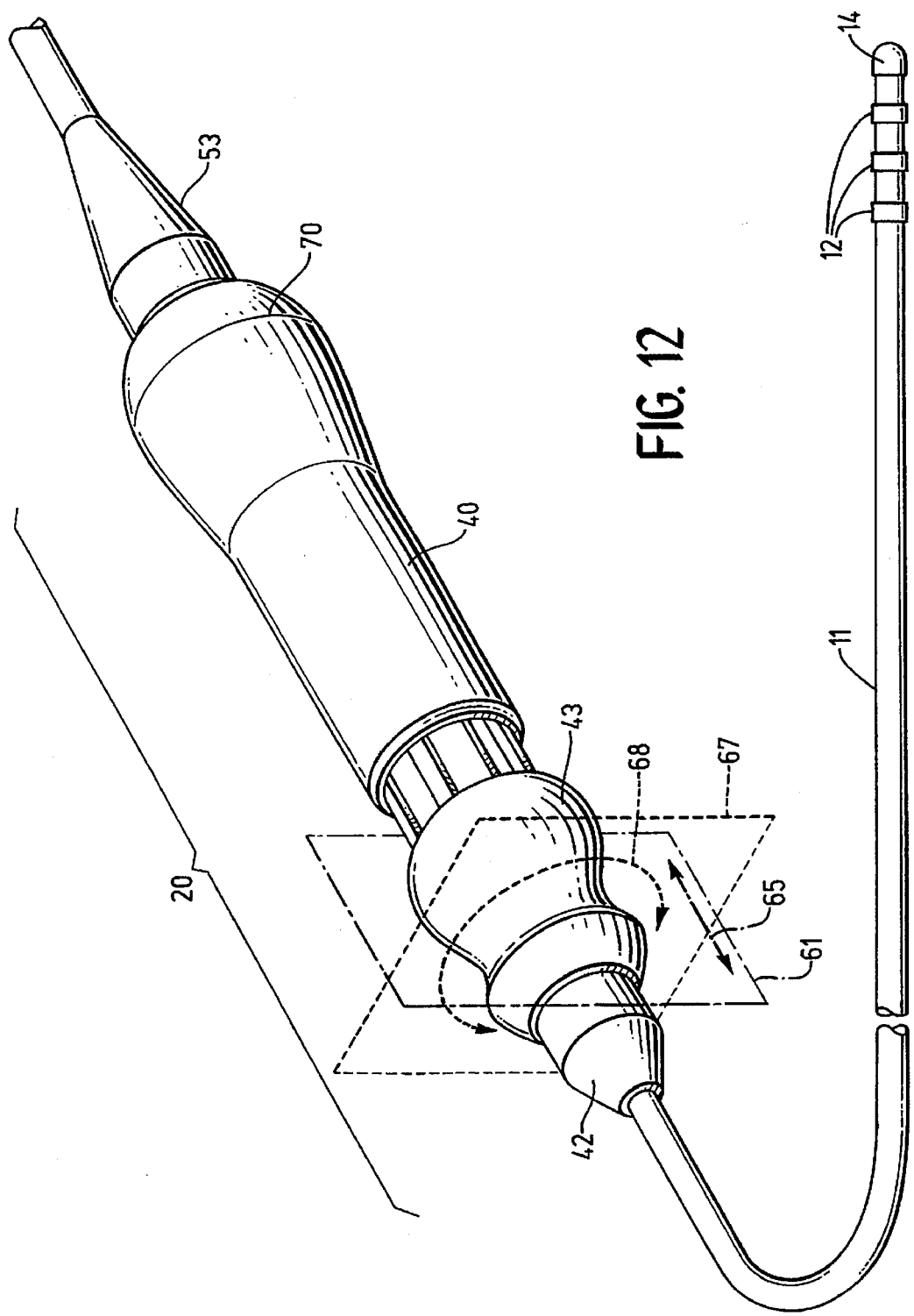
FIG. 12 is a perspective view of the catheter shown in FIG. 1.

Turning briefly to FIG. 12, the movement of the knob 43 in two planes can be seen. In the first plane 62, the knob 43 slides in a direction parallel to the longitudinal axis of the catheter 20 for control over the deflecting wire 23, as shown by the arrows 65 drawn in parallel with the longitudinal axis. In the second plane 66, the knob 43 rotates as shown by the curved arrows 68, to control the position of the stiffening member. These planes are perpendicular to each other in this view. It may also be noted that the handle body 40 includes a larger diameter portion 70 at its proximal end. The body 40 is smoothly tapered up to that enlarged diameter portion 70. The existence of this enlarged portion 70 provides a physical indicator to the physician as to the location of his or her hand on the handle 40. The physician can tell how far back his or her hand is on the handle based on the feeling imparted to the hand by the differences in diameter along the handle.

The cap 42 or female threaded element 44 may include indicia, such as the color red, placed at a certain point on its outer surface to establish a position reference system. Upon moving the slide element 43 far enough distally to reveal the red indicia on the cap, the operator would then be made aware that he or she has reached a predetermined position. Alternately, the indicia may include gradations marked on the cap.

Electrical conductors 16 and 17 (not shown in FIG. 8 or 9) pass through the inner lumen 52 of the tubular shaft 41 and are electrically connected to the electrical connector 53 shown on the proximal end of the handle 20 in FIG. 8. A suitable connector 53 is the Model NO. V114RC72 sold by Alden Products Company, located in Brockton, Mass. Other suitable electrical connectors are commercially available.

In one presently preferred embodiment of the invention, the tubular sheath member 24 about the deflection wire 23 has an outer diameter of about 0.015 to about 0.020 inches (0.38 to 0.51 mm) and an inner diameter of about 0.008 to about 0.012 inches (0.20 to 0.31 mm). The layer 27 formed of multifilament strands 28 and polymer matrix 29 has a wall thickness of about 0.003 to about 0.005 inches (0.08 to 0.013 mm) and the outer jacket or coating 26 has a wall thickness of about 0.004 to 0.007 inches (0.10 to 0.18 mm). The outer diameter of the catheter may range from about 0.079 to about 0.12 inches (2.01 to 3.05 mm) and the overall length of the catheter 10 may range from about 39.4 to 51.2 inches (100 to about 130 cm). The sensing electrodes 12 on the distal end are preferably formed of platinum or a platinum alloy and are about 0.030 to 0.079 inches (0.75 to about 2.0 mm) in with and are spaced along the length of the distal portion about 0.079 to 0.394 inches (2 to about 10 mm) apart. A preferable spacing is about 0.20 inches (5 mm). The ablution electrode which is about 0.16 inches (4 mm) long is also preferably formed of platinum or a platinum alloy, or platinum coated stainless steel.

The inner tubular member 25 is formed from a thermoplastic elastomer having a Shore hardness from about 75A to about 75D, preferably about 85A to about 55D and is preferably a thermoplastic polyurethane. Suitable polyurethanes include Tecothane® which is available from Thermedics, Inc. Alternative materials include Pebax® which is a thermoplastic elastomer available from the Atochem Company. The polymer matrix 29 is formed of a thermosetting polymer and preferably is an epoxy adhesive such as FDA2. The multi-filament strands 28 may be formed of high strength polymeric materials such as aramid (Kevlar®) available from E. I. duPont, deNemours & Co., Inc. The fibrous strands compress into a ribbon-like shape when braided.

The outer jacket or coating 26 is preferably formed of a thermoplastic polymeric material having a Shore hardness of about 85A to about 75D, preferably about 95A to about 65D. Suitable polymers include a polyurethane made with a polytetramethylene glycol ether which is available commercially as 2363 55DE Pellethane from the Dow Chemical Company or a polyurethane such as TT 2055D B320 Tecothane which is available from Thermedics. Other suitable thermoplastic polymeric materials may be employed.

Both the inner tubular member 25 and the outer jacket 26 may have incorporated therein a radiopaque material such as barium sulfate to facilitate the fluoroscopic observation during the procedure by the physician in attendance.

The electrical conductors 16 and 17 may be 30–40 awg copper wires with a suitable insulation, such as a polyamide, polyurethane/nylon, or a fluoropolymer such as poly (tetrafluoro)ethylene. The deflection wire 23 and stiffening member 31 are formed of a stainless steel suitable for in vivo use. The deflection wire 23 is about 0.005 to about 0.010 inch (0.127 to 0.254 mm) in diameter and the stiffening member 31 is about 0.010 to about 0.020 inch (0.254 to 0.508 mm) in diameter, and the lengths thereof are appropriate for the catheter in which they are utilized.

The catheter 10 can be conveniently made by the following procedure. Multi-filament strands 28 are braided about the inner tubular member 25 along the length thereof. The braiding may be terminated short of the distal portion 13 or the entire length of the inner tubular member 25 may be braided and the braided portion on the distal portion 13 may be removed. Matrix 29 is formed either by impregnating the braided product with a suitable impregnate or incorporating matrix material with the strands prior to braiding and then heating the braided product to form the matrix. To complete the catheter body member, a heat shrinkable thermoplastic tubular member or sleeve which forms the outer jacket 26 is fitted onto the braided and impregnated reinforcing layer 27, and then a heat shrinkable tubular element (not shown) is fitted over the thermoplastic tube forming the outer jacket 26 and the assembly is then heated by hot air to shrink the heat shrinkable tube and press the thermoplastic tube against the exterior of the reinforcing layer 27 to secure the jacket 26 thereto. Upon cooling, the heat shrinkable tube is stripped off and discarded and the catheter is then ground to the desired outer diameter.

Electrical conductors 16 and 17 are advanced through the inner lumen 15 of the inner tubular member 25 and electrically connected by soldering to the sensing electrodes 12 and the ablation electrode 14 respectively. The electrodes 12 are slid over the distal position 13 and secured to the exterior thereof by a suitable adhesive. Ablation electrode 14 is similarly secured to the distal tip of the catheter after conductor 17 is soldered thereto. The stiffening member 31 is passed proximally through the inner lumen 15 and is secured by its proximal end to the inward projection 48 on the male threaded element 47 on the manipulating handle 20 by suitable means such as brazing or soldering or by an adhesive. The deflection wire 23 is advanced through the lumen 21. The proximal end of the deflection wire 23 is secured by the same or similar means to the inward projection 51 on the ring 49. The distal end of the deflection wire 23 is secured by the same or similar means to the anchor plate 19 as shown in FIG. 10. In this instance a transverse slit is formed in the distal portion 13, the anchor plate 19 is adhesively bonded to the proximal facing of the slit and then the distal facing of the slit is adhesively bonded to the anchor plate and the proximal facing of the slit. An alternative embodiment is shown in FIG. 11 wherein an anchor cylinder 55 is provided which encircles and is secured to the inner tubular member 25, and has a linear depression or groove 56 which is seated into the open channel 30. In the latter instance, the deflection wire 23 is suitably secured such as by soldering within the groove 56. The anchor plate 19 and the anchor cylinder 55 may be formed of suitable high strength material such as stainless steel.

While the invention has been described herein in terms of certain preferred embodiments, those skilled in the art of catheters for performing electrophysiological procedures within a patient will recognize that various modifications and improvements can be made to the invention without departing from the scope thereof. Although preferred and alternative embodiments of the invention have been described and illustrated, it is clear that the invention is susceptible to numerous modifications and adaptations within the ability of those skilled in the art and without the exercise of inventive faculty. Thus, it should be understood that various changes in form, detail and usage of the present invention may be made without departing from the spirit and scope of the invention.

What is claimed is:

1. A catheter comprising:
a body member having a distal end and a proximal end;
a deflection control line slidable in a direction parallel to the longitudinal axis of the body member, the control line having a distal end attached to the body member wherein movement of said deflection control line controls deflection of the distal end of the body member; and
a stiffening member disposed within the body member and slidable in a direction parallel to the longitudinal axis of the body member, said stiffening member providing increased rigidity to the portion of the body member in which the stiffening member is located.

2. The catheter of claim 1, further comprising a movable control device mounted to the body member and connected to the stiffening member, and further being adapted for a range of selective movement in relation to the body member, wherein selective movement of the control device controls the position of the stiffening member in the body member.

3. The catheter of claim 2, wherein the control device is adapted for rotational movement wherein selective rotational movement of the control device controls the position of the stiffening member in the body member.

4. The catheter of claim 2, further comprising a handle connected to the proximal end of the body member wherein the movable control device is mounted to the handle and has a plurality of positions within its range of selected movement, wherein the handle comprises indicia formed on said handle and located within the range of selected movement of the control device to indicate the position of the control device.

5. The catheter of claim 4, wherein the indicia indicate the sliding position of the control device.

6. The catheter of claim 4, wherein said indicia comprise gradations.

7. The catheter of claim 4, wherein said indicia comprise a colored band to indicate movement of the control device beyond a preselected position.

8. The catheter of claim 4, wherein the indicia indicate the rotational position of the control device.

9. The catheter of claim 1, further comprising a movable control device mounted to the body member and further being adapted for a range of selective movement in relation to the body member, wherein the deflection control line has a distal end fixedly attached to a distal portion of the body member and a proximal end attached to the control device so that tension applied to the control line by selective movement of the control device will cause deflection of the distal portion of the catheter.

10. The catheter of claim 9, wherein the control device is adapted for a range of selective movement in relation to the body member and the control device is mounted to a proximal end of the stiffening member wherein selective movement of the control device controls the position of the stiffening member in the body member.

11. The catheter of claim 10, wherein the control device is adapted for selective simultaneous sliding and rotating movement.

12. The catheter of claim 11, wherein the stiffening member is connected to the control device such that rotating movement of the control device controls the position of the stiffening member in the body member.

13. The catheter of claim 12 wherein sliding movement of the control device controls the tension applied to the control line.

14. The catheter of claim 11 wherein sliding movement of the control device controls the tension applied to the control line.

15. The catheter of claim 9 wherein sliding movement of the control device controls the tension applied to the control line.

16. The catheter of claim 9 further comprising a handle connected to the proximal end of the body member wherein the control device is mounted to the handle and has a plurality of positions within its range of selected movement, wherein the handle comprises indicia formed on said handle and located within the range of selected movement of the control device to indicate the position of the control device.

17. A catheter comprising:
a body member having a distal end and a proximal end;
a deflection control line disposed within the body member and slidable in directions parallel to the longitudinal axis of the body member, wherein movement of said deflection control line controls deflection of the distal end of the body member;
a stiffening member disposed within the body member and slidable in directions parallel to the longitudinal axis of the body member, said stiffening member providing increased rigidity to the portion of the body member in which the stiffening member is located;
a handle connected to the proximal end of the body member; and
a movable control device adapted for selective movement, wherein the movable control device is mounted to the handle and has a plurality of positions within a range of selected movement,
wherein the handle comprises indicia formed on said handle and located within the range of selected movement of the control device to indicate the position of the control device.

18. The catheter of claim 17, wherein said indicia comprises visible gradations.

19. The catheter of claim 17, wherein said indicia comprises a colored band to indicate movement of the control device beyond a preselected position.

20. The catheter of claim 17, wherein the control device is adapted for selective simultaneous sliding and rotating movement.

21. The catheter of claim 20, wherein the indicia indicates the rotational position of the control device.

22. The catheter of claim 20, wherein the indicia indicates the sliding position of the control device.

23. A catheter comprising:

an elongated body member having a distal portion and a proximal portion;

an elongated first device movably mounted in said body member, movement of said first device providing selectively varying stiffness of the body member in accordance with the location in the body member of the first device; and an elongated second device movably mounted in said body member, movement of said second device in relation to the body member providing independent selectively variable deflection of the distal portion of the body member in accordance with said movement.

24. The catheter of claim 23, further comprising a movable control device mounted to the body member and connected to the first and second devices and being adapted for selective movement, wherein selective movement of the control device in a first direction variably controls the position of the first device thereby controlling stiffness of the body member, and selective movement of the control device in a second direction independently controls the position of the second device thereby controlling said deflection of the distal portion of the body member.

25. The catheter of claim 24, wherein the control device is adapted for selective simultaneous sliding and rotating movement.

26. The catheter of claim 25, wherein sliding movement of the control device controls the stiffness of the body member, and rotational movement of the control device controls the deflection of the distal portion of the body member.

27. The catheter of claim 23, further comprising a handle connected to the proximal end of the elongated body member;

wherein the movable control device is mounted to the handle and has a plurality of positions within a range of selected movement, wherein the handle comprises indicia formed on said handle and located within the range of selected movement of the control device to indicate the stiffness of the body member.

28. The catheter of claim 27, further comprising indicia formed on the handle to indicate the deflection of the distal portion of the body member.

29. A catheter comprising:

a body member having a distal end and a proximal end;

a stiffening member disposed within the body member and slidable in a direction parallel to the longitudinal axis of the body member, said stiffening member providing increased rigidity to the portion of the body member in which the stiffening member is located; and a rotatable control device adapted for selective rotation, wherein the stiffening member is connected at its proximal end to the control device such that rotating movement of the control device controls the position of the stiffening member in the body member.

30. The catheter of claim 29, further comprising a handle connected to the proximal end of the body member;

wherein the control device is mounted to the handle and has a plurality of positions within a range of selected movement;

wherein the handle comprises indicia formed on said handle and located within the range of selected movement of the control device indicating the position of the stiffening member in the body member.

* * * * *